United States Patent [19]

Bahrmann et al.

[11] 4,258,214

[45] Mar. 24, 1981

[54] PROCESS FOR THE PRODUCTION OF ALDEHYDES

[75] Inventors: Helmut Bahrmann, Hünxe; Boy Cornils, Dinslaken; Gerhard Diekhaus, Oberhausen; Waldemar Kascha, Oberhausen; Jürgen Weber, Oberhausen, all of Fed. Rep. of Germany

[73] Assignee: Ruhrchemie Aktiengesellschaft, Oberhausen, Fed. Rep. of Germany

[21] Appl. No.: 60,561

[22] Filed: Jul. 25, 1979

[30] Foreign Application Priority Data

Jul. 31, 1978 [DE] Fed. Rep. of Germany ....... 2833538

[51] Int. Cl.³ ............................................ C07C 45/50
[52] U.S. Cl. ................................................... 568/454
[58] Field of Search ................. 260/604 HF; 568/909, 568/454; 252/431 P

[56] References Cited

U.S. PATENT DOCUMENTS

| | | | |
|---|---|---|---|
| 3,239,566 | 3/1966 | Slaugh | 260/604 HF |
| 3,518,319 | 6/1970 | Ellert et al. | |
| 3,527,809 | 9/1970 | Pruett et al. | 260/604 HF |
| 3,535,400 | 10/1970 | Falbe et al. | 260/604 HF |
| 3,821,311 | 6/1974 | Hughes et al. | 260/604 HF |
| 3,917,661 | 11/1975 | Pruett et al. | 260/410.9 R |
| 3,954,877 | 5/1976 | Gipson | 260/604 HF |
| 3,994,978 | 11/1976 | Whitehurst | 260/604 HF |
| 4,041,082 | 8/1977 | Onoda et al. | 260/604 HF |
| 4,137,240 | 1/1979 | Peterson | 260/604 HF |

FOREIGN PATENT DOCUMENTS 1793069 7/1968 Fed. Rep. of Germany ........... 568/454

OTHER PUBLICATIONS

Tolman, J. Amer. Chem. Soc., vol. 92, pp. 2953-2956 (1970).

*Primary Examiner*—Werren B. Lone
*Attorney, Agent, or Firm*—Sprung, Felfe, Horn, Lynch & Kramer

[57] ABSTRACT

A process for the preparation of an aldehyde of the formula R—CH(CH$_3$)—CHO where R is a straight-chain alkyl group having 7 to 12 carbon atoms by reaction of an olefin of the formula R—CH=CH$_2$ where the carbon monoxide and hydrogen is described, the process being carried out in the presence of a complex phosphine containing rhodium compound as catalyst. After the reaction has been performed the reaction product is subjected to a thermal treatment at 100° to 190° C., if desired after previous separation of the catalyst.

9 Claims, No Drawings

PROCESS FOR THE PRODUCTION OF ALDEHYDES

BACKGROUND OF THE INVENTION

1. Field of the Invention

The present invention relates to a process for the production of aldehydes of the general formula R—CH(CH$_3$)CHO by reacting olefins of the general formula R—CH=CH$_2$ with carbon monoxide and hydrogen at an elevated temperature and elevated pressure in the presence of rhodium complex catalysts containing phosphine.

2. Discussion of the Prior Art

The so-called Oxo synthesis (hydroformylation) is widely used in industry for the preparation of aldehydes and alcohols. Cobalt which is active in the form of its carbonyl compounds is used above all as catalyst for the reaction of the olefin with carbon monoxide and hydrogen on a commercial scale.

More recently, rhodium complex catalysts in which biphilic ligands such as tertiary phosphines are coordinated the rhodium atom are used for the hydroformylation, especially for the hydroformylation of specific olefins. Rhodium catalysts are characterized by high selectivity for the formation of straight-chain aldehydes and permit the reaction to be carried out under a lower pressure than in conventional processes.

According to German Offenlegungsschrift (DOS-OS) No. 17 93 069, oxygen-containing products which are rich in normal aldehydes are prepared by reacting an α-olefin compound with carbon monoxide and hydrogen in the presence of a catalystic amount of a complex catalyst which consists substantially of rhodium complexed with carbon monoxide and a ligand which contains a trivalent atom of a Group V element, said atom being substituted with three organic radicals. The ligand is characterized inter alia in that it exhibits a free electron pair and has a Δ-HNP value of at least 425 and preferably at least 500. The Δ-HNP value is a measure of the basicity of the ligand, high basicity corresponding to a low Δ-HNP value. The reaction is carried out at 50° to 145° C. and a total pressure of carbon monoxide and hydrogen of less than about 31.5 atmospheres gauge.

The advantages of the oxo reaction catalyzed by rhodium complex compounds, especially the use of low pressure and high yields of straight-chain aldehydes, are offset inter alia by the requirement to use large reaction spaces and the difficulty to recover aldehydes which are methyl-branched in alpha position in satisfactory yields at high purity.

It is an object of this invention, therefore, to provide a process by means of which higher aldehydes which are branched in alpha-position, i.e., aldehydes having at least 10 carbon atoms can be prepared in a simple manner.

SUMMARY OF THE INVENTION

It has now been found that aldehydes of the general formula R—CH(CH$_3$)—CHO wherein R is a straight-chain alkyl group having 7 to 12 carbon atoms can be obtained by contacting an olefin of the general formula R—CH=CH$_2$ wherein R is as defined above with carbon monoxide and hydrogen at 80° to 170° C. and 200 to 250 bars in the presence of complex phosphine rhodium compounds as catalysts is soluble in said olefin, carbon monoxide and hydrogen, and thereafter subjecting the reaction product to a thermal treatment at 100° to 190° C.

The complex phosphine rhodium catalyst can be prior formed by reaction of a rhodium salt with an organic phosphine or it can be formed in situ by reaction of the rhodium salts with the organic phosphine in the reaction mixture containing the olefin.

If desired, the thermal treatment at 100°–190° C. can be preceded by separation of the catalyst.

The new process represents a simple route for recovering the α-branched aldehydes from a reaction mixture which contains normal (straight-chain) aldehydes and aldehydes which are methyl-branched in alpha position. The hydroformylation under the conditions according to the invention ensures that the starting olefin is reacted with a high yield, at a high reaction rate and with a high space-time yield to a mixture of unbranched aldehydes and those which contain a methyl group in α-position. The two isomeric aldehydes are resolved in a simple manner by the thermal aftertreatment. Surprisingly, the straight-chain aldehydes having the number of carbon atoms mentioned above are converted by heating to 100° to 190° C. into higher molecular weight condensation products while the α-methyl-branched aldehydes are preserved unchanged.

Mixtures containing carbon monoxide and hydrogen generally in a ratio by volume of 1:4 to 4:1 and especially 1:2 to 2:1 are used for the reaction of the olefins.

The reaction is advantageously carried out at temperatures of 80° to 170° C. and pressures to 200 to 350 bars. Temperatures of 100° to 150° C. and pressures of 200 and 270 bars have been found to be particularly advantageous.

Complex rhodium compounds which contain organic phosphines as ligands in addition to carbon monoxide and hydrogen are used as catalysts. These complex compounds are added to the reaction mixture either in preformed form or formed under the reaction conditions from rhodium salts which are soluble in the olefin, organic phosphines, carbon monoxide and hydrogen. Usually, the catalyst is present in a concentration of 20 to 100 ppm of rhodium, calculated as metal and based on olefin charged. Rhodium salts of fatty acids, i.e., carboxylic acids having at least 6 to 20 carbon atoms, are especially used as rhodium compounds which are converted in situ into the rhodium complex. Examples of such salts include Rh-2-ethyl hexanoate, Rh-stearate and Rh-oleate.

Organic phosphines the electron donor-acceptor behavior of which is characterized by an $\Sigma_{\chi_i}$-value between 0 and 14 are used with particular success as complex ligands. The importance of the $\Sigma_{\chi_i}$-value for homogeneously catalyzed reactions is described in greater detail in the paper by Chadwick A. Tolman in Journal of the American Chemical Society 92 (1970), pp. 2953–2956, the disclosure of which is hereby incorporated herein by reference. Phosphines with the properties mentioned above include especially trialkyl e.g., C$_3$ to C$_{18}$ alkyl phosphines, e.g., triethyl phosphine, tributyl phosphine, trioctyl phosphine and triphenyl phosphine. Triarylphosphites such as triphenylphosphit are disclosed.

Rhodium complexes which contain phosphine in addition to carbon monoxide and, if necessary, hydrogen are more stable than those complexes which are built up only of rhodium, carbon monoxide and, if desired, hydrogen. To obtain a catalyst having sufficient stability, the phosphine is, therefore, preferably used in an excess so that at least 50 moles of phosphine are present in the reaction mixture per gram atom of rhodium. The use of 50 to 200 moles of phosphine per gram atom of rhodium has been found to be particularly useful.

The reaction can be carried out without the concomitant use of additional solvents. In this case, the starting olefins and the phosphine serve as reaction medium. However, the reaction can also be carried out in a solvent, examples of suitable solvents including aromatic hydrocarbons such as benzene, toluene, xylene or higher aliphatic hydrocarbons such as pentane, hexane, and, moreover, ethers or alcohols.

When reacting olefins of the general formula $R-C^{\beta}H=C^{\alpha}H_2$ with carbon monoxide and hydrogen, the hydroformylation takes place preferentially in α-position, i.e. straight-chain aldehydes primarily obtained. If the formyl group enters in β-position, methyl-branched aldehydes are formed. Normally the reaction mixture consists under the reaction conditions mentioned above of about 60 percent by weight of straight-chain aldehyde and about 40 percent by weight of branched aldehydes. In addition to aldehydes which contain a methyl group in α-position, larger amounts of further isomers formed by migration of the double bond are produced by hydroformylation of the internal olefins formed by isomerization of the double bond.

It has been found surprisingly that if rhodium catalyts containing organic phosphines having a $\Sigma_{\chi_i}$-value between 0 and 5 as complex liquids are used, the migration of the double bond in the starting olefin is completely suppressed so that exclusively the aldehyde having the same number of carbon atoms with a methyl group in α-position to the carbonyl group is formed in addition to the straight-chain aldehyde. Resolution of the two isomeric aldehydes is successfully achieved by a thermal treatment of the reaction product carried out subsequently to the actual synthesis. It may be preceded by separation of the catalyst by known methods, e.g., by reaction of the reaction mixture with hydrogen or steam.

For the thermal treatment, the reaction mixture is simply heated to temperatures between 100° and 190° C. This heating may be effected separately but is more advantageously combined with the distillation of the reaction mixture. In this case, the mixture coming from the synthesis is passed to a distillation column and heated to the appropriate temperatures thereby distilling off the branched aldehydes while the straight-chain aldehydes are converted by condensation into compounds which are not readily volatilized and remain in the bottoms of the column.

The process according to the invention is carried out, for example, by giving the olefin together with a rhodium salt and a phosphine and, if desired, with a solvent into a reactor and reacting it with carbon monoxide and hydrogen under the temperature and pressure conditions described above. The reaction may also be carried out continuously in suitable apparatus. After cooling and depressurization of the reaction product, the superfluous gas mixture is separated and the reaction mixture subjected to the thermal treatment.

The α-methyl-alkyl aldehydes obtainable by the process according to the invention are used as components of perfume compositions.

In the examples which follow, the process according to the invention is illustrated:

EXAMPLE 1

Hydroformylation of n-undecene-1

In an autoclave of stainless steel, 750 g. (4.77 moles) of n-decene-1 are reacted with carbon monoxide and water ($CO:H_2 = 1:1$) in the presence of 18.4 mg. (0.18 mmoles) of rhodium in the form of rhodium-2-ethyl hexanoate and 3.5 g. (17.3 mmoles) of tri-n-butyl-phosphine at 130° C. and 270 bars. After about 1.5 hours when no more gas is absorbed, the autoclave with the reaction product is cooled to room temperature. The subsequent processing by distillation in a 36 plate column at 10 Torr at an overhead temperature of 120° C. and a bottoms temperature of 170° C. gives 314 g. of 2-methyl undecanal corresponding to a yield of 35 percent based on n-undecene-1 charged.

The 2-methyl undecanal has a purity of more than 98 percent determined by gas chromatography.

EXAMPLE 2

Hydroformylation of n-decene-1

In an autoclave of stainless steel, 736 g. (5.25 moles) of n-decene-1 are hydroformylated with the same amounts of catalyst and under the same reaction conditions as in Example 1. The reaction is completed after 2 hours. The autoclave is cooled and the reaction mixture distilled in a column having 36 plates at 10 Torr. 268 Grams of 2-methyl decanal corresponding to a yield of 30 percent based on decene distil at an overhead temperature of 110° C. and a bottoms temperature of 145° C. The product has a purity of more than 98 percent determined by gas chromatography.

What is claimed is:

1. A process for preparing an aldehyde of the general formula $R-CH(CH_3)-CHO$ where R is a straight-chain alkyl group having 7 to 12 carbon atoms which comprises contacting an olefin of the formula $R-CH=CH_2$ wherein R is a straight-chain alkyl group having 7 to 12 carbon atoms with carbon monoxide and hydrogen at 80° to 170° C. under a pressure of 200 to 350 bars in the presence of a complex phosphine containing rhodium compound and thereafter subjecting the reaction product to thermal treatment at 100° to 190° C.

2. A process according to claim 1 wherein preformed rhodium phosphine containing complex is introduced into a reaction mixture comprising said olefin.

3. A process according to claim 1 wherein said complex phosphine containing rhodium compound is formed in situ in the reaction mixture by reaction of a rhodium salt soluble in said olefin and an organic phosphine.

4. A process according to claim 1 wherein the complex phosphine containing rhodium compound is separated from the reaction product prior to said thermal treatment.

5. A process according to claim 3 wherein said rhodium salt is a rhodium salt of an organic carboxylic acid having at least 6 carbon atoms.

6. A process according to claim 3 wherein said organic phosphine is one having $\Sigma_{\chi_i}$-value of 0 to 14.

7. A process according to claim 6 wherein said organic phosphine has a value $\Sigma_{\chi_i}$-value of 0 to 5.

8. A process according to claim 3 wherein there are at least 50 moles of organic phosphine per gram atom of rhodium.

9. A process according to claim 8 wherein there are 50 to 200 moles of organic phosphine per gram atom of rhodium.

* * * * *